United States Patent [19]

Grafius

[11] Patent Number: 5,146,713
[45] Date of Patent: Sep. 15, 1992

[54] HYDRAULIC DOOR OPERATING SYSTEM FOR AUTOCLAVES AND STERILIZERS

[75] Inventor: Gerald R. Grafius, Erie, Pa.

[73] Assignee: American Sterilizer Company, Erie, Pa.

[21] Appl. No.: 695,051

[22] Filed: May 2, 1991

[51] Int. Cl.$^5$ .............................................. E05F 7/02
[52] U.S. Cl. ...................................... 49/255; 49/477; 49/506
[58] Field of Search ................. 49/255, 254, 256, 260, 49/477, 506; 269/32

[56] References Cited

U.S. PATENT DOCUMENTS

| | | | |
|---|---|---|---|
| 3,371,986 | 3/1968 | Brown | 49/477 X |
| 3,888,045 | 6/1975 | Piegza | 49/255 |
| 4,469,335 | 9/1984 | Moore | 49/477 X |
| 4,511,127 | 4/1985 | Schron et al. | 269/32 |
| 4,545,149 | 10/1985 | Jentsch | 49/255 |
| 4,818,001 | 4/1989 | Pisacane et al. | 49/255 X |
| 4,932,160 | 6/1990 | Sperko | 49/254 |
| 4,986,032 | 1/1991 | Wessiepe et al. | 49/477 |

Primary Examiner—Philip C. Kannan
Attorney, Agent, or Firm—Kirkpatrick & Lockhart

[57] ABSTRACT

An apparatus and method are described for opening, closing, and sealing the door of a sterilizer. The apparatus includes a clamping device for compressing a compressible gasket between the door and the chamber of the sterilizer, and the clamping device can provide variable clamping pressure. Further, the clamping device is self-locking and once in a clamped position it requires the positive application of hydraulic pressure to move it to an unclamped state. The apparatus also includes hydraulic mechanisms for opening and closing the door and raising and lowering the door against the face of the sterilizer. Each of these hydraulic mechanisms may be adjusted to vary the amount of force used to open and close the door or to raise and lower the door. In addition, the hydraulic mechanisms used for clamping the door, opening and closing the door, or raising and lowering the door are adapted so that they can be operated during a loss of electrical power.

23 Claims, 4 Drawing Sheets

HYDRAULIC DOOR OPERATING SYSTEM FOR AUTOCLAVES AND STERILIZERS

BACKGROUND OF THE INVENTION

1. Field of the Invention

The invention relates to closure systems and methods for releasably sealing autoclaves and sterilizers. More particularly, the invention relates to a variable pressure, hydraulically actuated door clamping system for an autoclave or sterilizer door which is also self-locking. In addition, the invention relates to a variable pressure, hydraulically actuated system for positioning the autoclave door between open and closed positions and also vertically positioning the door so that the clamping system is engaged.

2. Description of the Prior Art

The autoclave and sterilizer art generally describes apparatus and methods for releasably sealing doors of autoclaves and sterilizers. The ability of a particular apparatus to effectively seal a sterilizer is critical because the apparatus must maintain the temperature and pressure environment within the sterilizer to insure that effective sterilization takes place. Ineffective sterilization may result in contaminated equipment or articles which are subsequently used for medical procedures. The contaminated equipment or articles may in turn cause infection in patients. In addition, autoclave or sterilizer sealing apparatus must be operable in a safe manner by the person using the apparatus.

Generally, conventional sealing apparatus rely on a compressible gasket or a pressurized fluid to provide an effective seal between the door and the chamber. U.S. Pat. No. 4,932,160 describes an apparatus for sealing an autoclave door which includes both the use of a compressible gasket and a pressurized fluid. The compressible gasket is located in a gasket channel, and once the autoclave door is moved to a closed position the pressurized fluid is pumped into the gasket channel and forces the compressible gasket against the door to provide an effective seal. Other patents teach similar sealing apparatus which rely on the use of a pressurized fluid to provide an effective seal between the door and chamber of an autoclave or sterilizer. For example, U.S. Pat. Nos. 3,694,962; 3,371,986; 4,335,075 describe apparatus of this type. It should be appreciated that apparatus which rely on a pressurized fluid to provide the seal between a door and a chamber will correspondingly require a system for pressurizing and depressurizing that fluid. This fluid pressurizing and depressurizing system increases both the complexity and expense of the apparatus.

Conventional apparatus which rely on compressible gaskets to provide a seal between a door and chamber suffer from failure due to creep or permanent set of the gasket. Furthermore, conventional compressible gasket systems typically require expensive and mechanically complicated equipment for compressing the gasket between the door and chamber. (See U.S. Pat. No. 4,469,335 at col. 1, lines 46-50). It is believed that these disadvantages associated with compressible gaskets system were overcome by the use of the pressurized fluid sealing type systems.

Conventional sterilizer and autoclave door opening, closing, and sealing systems also suffer from problems associated with loss of electrical or hydraulic power. For example, in some conventional systems the loss of electrical or hydraulic power may cause the clamping part of the system to release thereby unsealing the autoclave or sterilizer. This type of failure could be particularly dangerous if the autoclave or sterilizer is in a pressurized state. A more frequently occurring problem relates to the inability to operate the autoclave or sterilizer when electrical or hydraulic power is lost. In addition, conventional opening and closing systems may allow the door to inadvertently move and close over time due to leakage in the hydraulic system.

Moreover, conventional autoclave and sterilizer opening, closing, and sealing systems suffer from the disadvantage that the force exerted to open or close the door of the autoclave or sterilizer is constant. The use of a constant force for this purpose may result in injury to the operators or other persons in proximity to the autoclave or sterilizer due to the amount of force exerted by the door.

SUMMARY OF THE INVENTION

The present invention provides an apparatus and method which is useful for opening, closing, and sealing an autoclave or sterilizer door. In particular, the present invention overcomes the disadvantages of conventional autoclave sealing systems which use compressible gaskets. The present invention is capable of adjusting to creep or permanent set in the gasket. Conventional sealing systems without this capability tend to lose the effectiveness of their seal.

Likewise, the present invention overcomes the disadvantages associated with systems which use a pressurized fluid because it uses a compressible gasket and compresses the gasket by the application of an adjustable force. The capability of the present invention to apply variable force is used to correct for creep or permanent set of the gasket. In this manner, the present invention provides a mechanically simple and effective seal by using a compressible gasket for sealing a door to a chamber.

In addition, the present invention overcomes the disadvantages of conventional autoclave and sterilizer sealing systems which relate to the loss of electrical or hydraulic power. The present invention provides a self-locking sealing system which cannot be unsealed without the application of positive hydraulic pressure. This insures that the apparatus of the present invention will maintain its seal when electrical or hydraulic power is lost.

Moreover, the present invention provides mechanisms for manually generating hydraulic pressure and activating the clamping system, the door opening and closing system, and the door raising and lowering system. Consequently, the apparatus of the present invention can be completely manually operated during any loss of electrical or hydraulic power.

The present invention generally comprises an apparatus for opening, closing and sealing a door of a chamber. The apparatus comprises a means for clamping the door to the chamber to provide an effective seal therebetween. The clamping means is capable of providing a variable force for clamping the door to the chamber. Preferably, a compressible gasket is provided between the door and the chamber to effect the seal therebetween.

Preferably, the clamping means comprises a plurality of extendable hydraulically driven pins which exert a mechanical force on lugs along the edge of the door towards a sealing face of the chamber and thereby compresses the gasket to provide an effective seal. The hydraulically driven pins are designed so that a positive hydraulic pressure is required to extend or retract the pins. In this matter, the hydraulically driven pins may be described as self-locking because once in an extended position, even if hydraulic pressure to the pin is lost, the pin cannot be retracted without the application of hydraulic pressure.

The apparatus also comprises a means for moving the door between an open position which allows loading of equipment and carts into the chamber and a closed position in which the door is positioned against the face of the chamber. Preferably, the means for moving the door between the open and closed positions includes the capability of varying the force used to move the door between the open and closed positions. In a preferred embodiment, a hydraulic cylinder is used to move the door between the open and closed positions, and the hydraulic pressure fed to the hydraulic cylinder can be varied as desired to vary the force exerted in opening and closing the door.

In addition, the apparatus comprises means for raising or lowering the door to engage the clamping means. The raising and lowering means is preferably capable of providing variable force for raising and lowering the door. Moreover, the raising and lowering means preferably comprises a hydraulic cylinder wherein the force exerted by the hydraulic cylinder is adjustable to vary the force used to raise or lower the door.

The apparatus additionally comprises a guiding means for guiding the door as it is lowered so that it effectively engages the hydraulically driven pins of the clamping means. The guiding means eliminates problems associated with the door getting hung up on the pins of the clamping means.

BRIEF DESCRIPTION OF THE DRAWINGS

The present invention can be better understood by reference to the drawings in which.

DETAILED DESCRIPTION OF THE PREFERRED EMBODIMENTS

Figure 1:
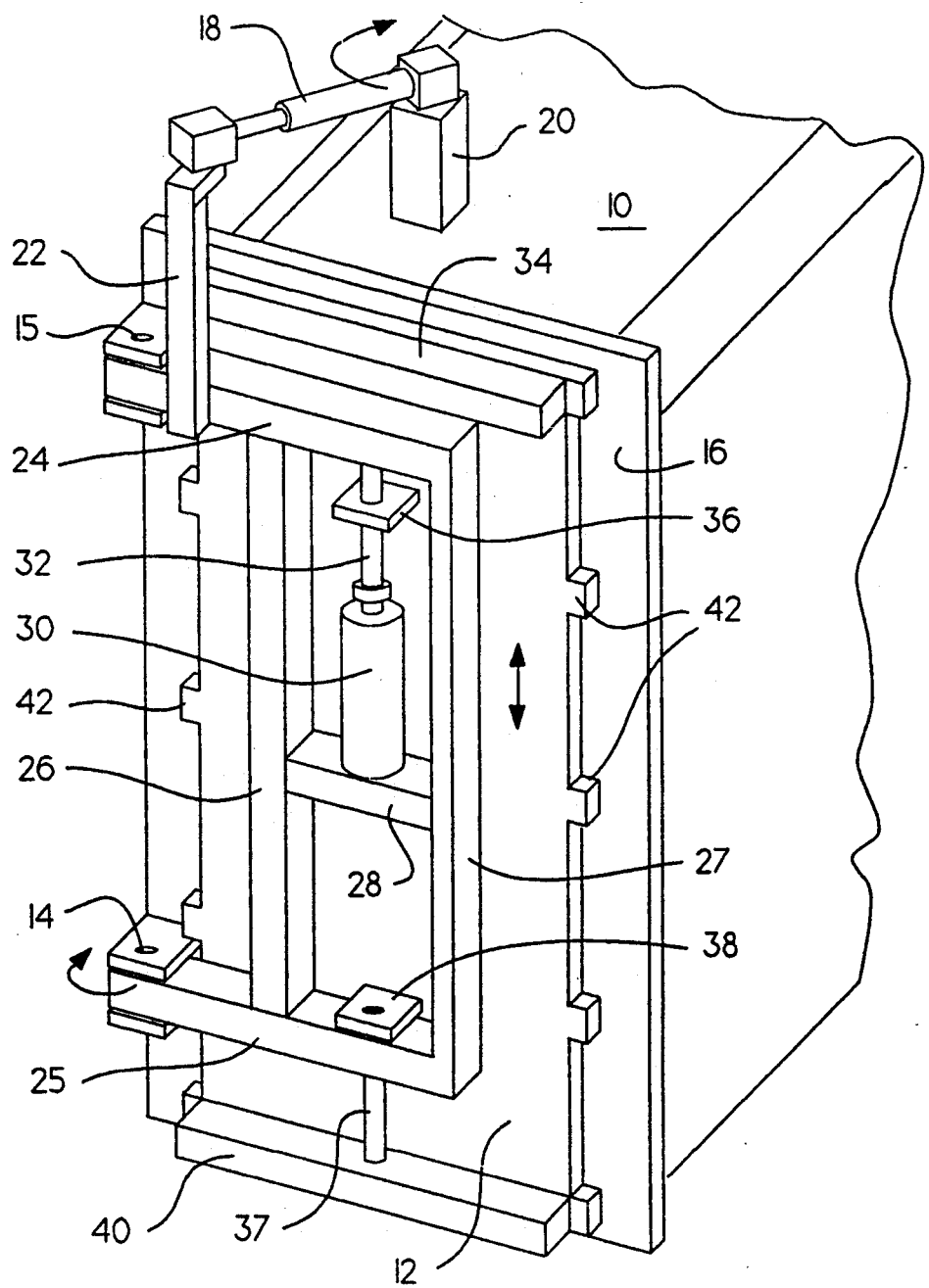
FIG. 1 is a perspective view of the apparatus of the present invention wherein the autoclave door is opened to the left.

Referring now to FIG. 1, an overall perspective view of the apparatus for opening, closing, and sealing a door of an autoclave or sterilizer is depicted. An autoclave or sterilizer chamber 10 and corresponding door 12 along with assemblies for opening, closing, and sealing the door 12 against the sealing face 16 of the chamber 10 are shown. The door 12 is pivotally mounted on the sealing face 16 by two hinges 14, 15. As shown in FIG. 1, the door 12 will open to the left because the hinges attach the door to the chamber on the left. It should be appreciated that the door could be opened to the right by attaching the door to the sealing face of the chamber using hinges on the right.

An open-close assembly is used to move the door 12 between an open position which allows access for loading the chamber 10 with carts and equipment to be sterilized and a closed position in which the door 12 is positioned against the sealing face 16. The open-close assembly includes an open-close hydraulic cylinder 18, a chamber pivot connector 20, and a door connector 22. Any conventionally available hydraulic cylinder with an extendable rod which will extend and retract by application of hydraulic pressure to the cylinder may be used as the open-close hydraulic cylinder 18. The amount of force exerted by the rod as it extends and retracts is proportional to the amount of hydraulic pressure supplied to the cylinder. In addition, the rod of the hydraulic cylinder must exert sufficient force to move the door.

One end of the open-close hydraulic cylinder 18 is pivotally attached to the chamber pivot connector 20 which is in turn attached to the top of the chamber 10. The open-close hydraulic cylinder 18 is oriented parallel to the top of the chamber 10 and pivots through a range of positions which are parallel to the top of the chamber 10. The end of the open-close hydraulic cylinder 18 which is distal to the chamber pivot connector 20 is pivotally attached to door connector 22. Connector 22 is in turn attached to a hinge member 24 which is attached to the sealing face 16 of the chamber 10 by hinge 15. As a result of this configuration of the open-close assembly, when hydraulic pressure is provided to the open-close hydraulic cylinder 18, the cylinder rod extends thereby causing the door 12 to open due to the mechanical force exerted on the door 12 by the rod of the open-close hydraulic cylinder 18.

A door frame assembly is used to connect the door 12 to the sealing face 16 by way of hinges 14 and 15. The door frame assembly includes two hinge members 24 and 25 which connect to hinges 14 and 15 and extend horizontally across the face of the door; and two vertical members 26 and 27 which vertically interconnect hinge members 24 and 25. The door frame assembly further includes a raise-lower hydraulic cylinder 30 and a cross member 28 between vertical members 26 and 27 for supporting the raise-lower hydraulic cylinder 30.

The door 12 includes bars 34 and 40 which are located horizontally at the top and the bottom of the door 12 and extend outwards from the face of the door 12. A rod 37 is attached at one end to bar 40. Rod 37 extends vertically from the bar 40 through a hole in hinge member 25 and through a guiding plate 38. In this manner the rod 37 may slide through the hole of hinge member 25 and guiding plate 38. Likewise, the raise-lower hydraulic cylinder 30 includes a rod 32 which extends through a guiding plate 36 and through a hole in the hinge member 24 and connects to the bar 34. In this manner the rod 32 can slide through the hinge member 24 and guiding plate 36. Guiding plates 36 and 38 are welded to the door 12. Any conventionally available hydraulic cylinder with an extendable rod which will extend and retract by application of hydraulic pressure to the cylinder may be used as the raise-lower hydraulic cylinder 30. The amount of force exerted by the rod as it extends and retracts is proportional to the amount of hydraulic pressure supplied to the cylinder. Further, the rod of the hydraulic cylinder must exert sufficient force to raise the door 12.

It should be appreciated that the raise-lower assembly and door frame assembly allow the door 12 to be raised and lowered through a range of positions relative to the sealing face 16 by application of hydraulic pressure to the raise-lower hydraulic cylinder 30. The maximum amount of vertical displacement when the door 12 is raised or lowered is determined by limit switches for the hydraulic circuit which operates the raise-lower cylinder rod 32.

The door further includes lugs 42 which are used to apply mechanical pressure to the door 12 to seal it against the sealing face 16 of the chamber 10. The clamping means for applying mechanical pressure to lugs 42 are not shown in FIG. 1 but are described below.

Figure 2:
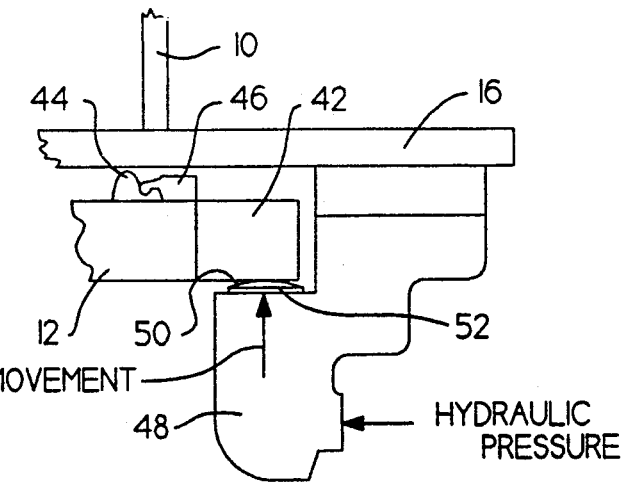
FIG. 2 is a section view of a clamping means of the present invention.

Referring now to FIG. 2, a cross-sectional view of the sealing and clamping means of the present invention are shown. In particular, the door 12 includes a compressible gasket 44 and a gasket retaining bar 46 which run continuously around the inside edge of the door 12. The compressible gasket 44 is parabolic shaped with a lip such that the flat side of the gasket 44 and the lip are positioned against the inside face of the door 12 and the curved side of the gasket 44 faces the sealing face 16. The gasket retaining bar 46 is attached to the door and includes a rib which extends over the lip of the gasket 44 and interlocks with the gasket 44. In this manner, the gasket 44 is maintained in position against the inside face of the door 12.

When force is applied to clamp the door 12 to the sealing face 16, the gasket 44 is compressed against the sealing face 16 such that the gasket 44 flattens out and provides an effective airtight seal between the door 12 and the sealing face 16. Consequently, a pressure differential can be maintained between the space inside of the sealed door and chamber and the surrounding atmosphere.

The clamping means includes multiple clamps 48 which are attached to sealing face 16. Each clamp 48 includes an extendable hydraulically driven pin 52 which contacts a door lug 42 on the door 12. When hydraulic pressure is applied to the clamp 48, it provides mechanical force to extend the pin 52 which in turn compresses the gasket 44 against the sealing face 16. The mechanical force exerted by the pin 52 against the door lug 42 is proportional to the amount of hydraulic pressure supplied to the clamp 48. Each clamp 48 includes a ramp 50 which is located adjacent to and vertically above the pin 52 of the clamp 48. The ramp 50 serves to align and move the door 12 against the sealing face 16 as the door 12 is vertically lowered so that the lugs 42 will engage the pins 52.

Preferably, the clamps as described herein are self-locking hydraulic clamping devices as described in Reissue U.S. Pat. No. 32,704, incorporated herein by reference. (This patent is a reissue of U.S. Pat. No. 4,511,127). In particular, the clamping devices described in these patents have the advantage of being self-locking such that even if hydraulic pressure fails the clamps will maintain their locked and clamped status. In addition, the self-locking clamps of these patents use a minimum amount of space.

The door 12 additionally includes "Vlier" pins which provide a pressure to displace the door a small amount from the sealing face 16 of the sterilizer. Once the door is unclamped, the force exerted by the "Vlier" pins pushes the door 12 away from the sealing face 16 thereby breaking the seal.

Figure 3:
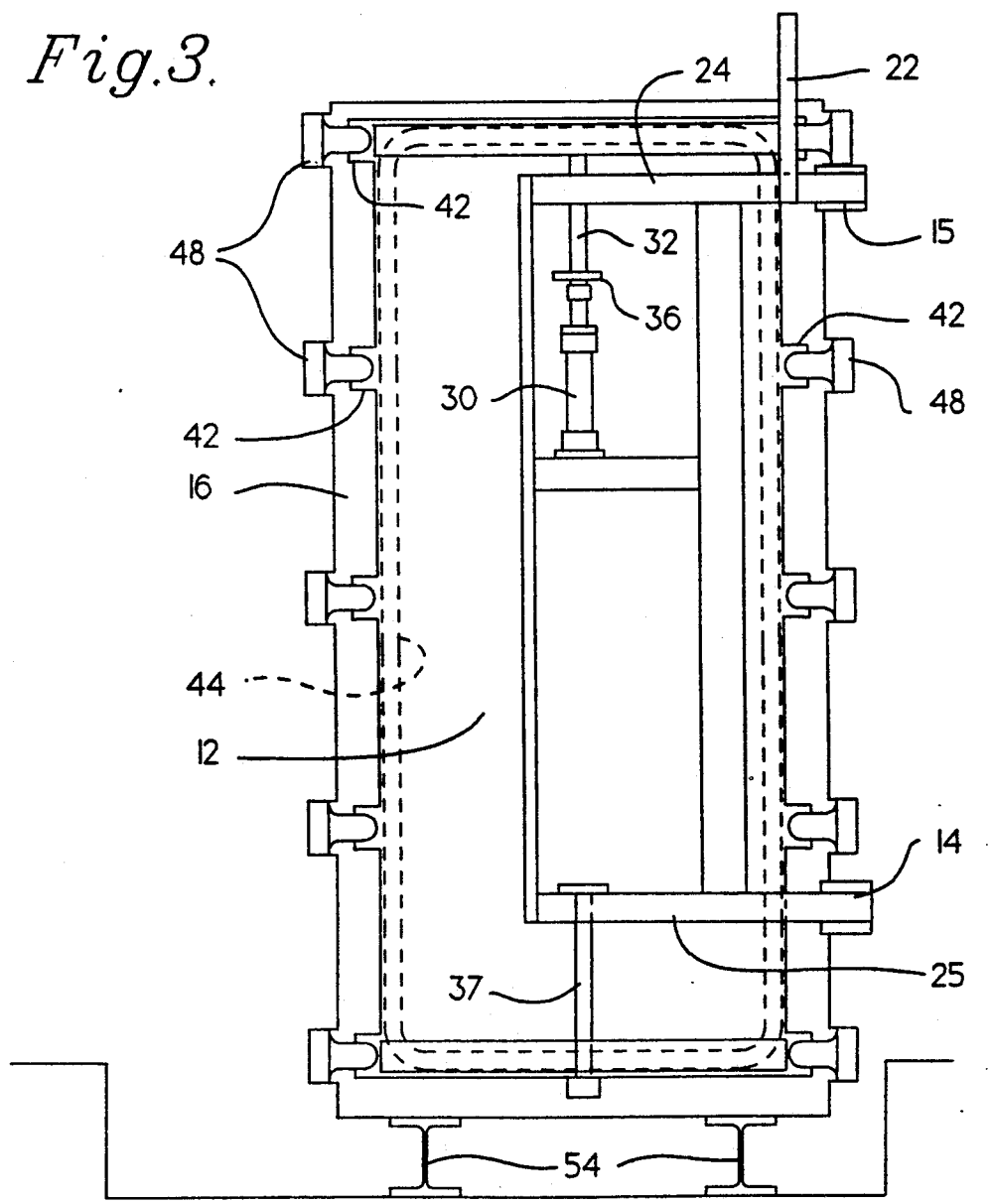
FIG. 3 is a front section view of a chamber and door when the door is in a closed and lowered position.

Referring to FIG. 3, a front view of a door in a closed and lowered position relative to a chamber is shown. The chamber is located in a pit but is supported above the bottom surface of the pit by support members 54. Typically I-beams may be used for this purpose. Sealing face 16 includes ten clamps 48 of the type disclosed in Reissue U.S. Pat. No. 32,704. Five of the clamps 48 are located on the left side of the sealing face 16, and the other five clamps 48 are located on the right side of the sealing face 16. Corresponding to the ten clamps 48 are ten lugs 42.

When the door 12 is in the lowered position, the lugs 42 are located between the clamps 48 and the sealing face 16. Consequently, when the clamps 48 are hydraulically actuated, the pins of the clamps 48 apply mechanical pressure to force the door 12 against the sealing face 16 such that the gasket 44 is compressed between the door 12 and the sealing face 16.

It should be appreciated that in the lowered position, the door 12 cannot be pivotally moved to an open position because the clamps 48 prevent the door from opening. In addition, in the lowered position, the bottom edge of the door 12 is located below the top edge of the pit. Thus, the top edge of the pit will prevent the door 12 from opening. Nevertheless, once the door 12 is raised, the lugs 42 are clear of the clamps 48 and the bottom edge of the door is above the top edge of the pit. The door can then be moved to an open position. It is desirable to locate the chamber in a pit so that equipment on wheeled trays can easily be rolled directly into the chamber without a change in elevation.

Figure 4A:
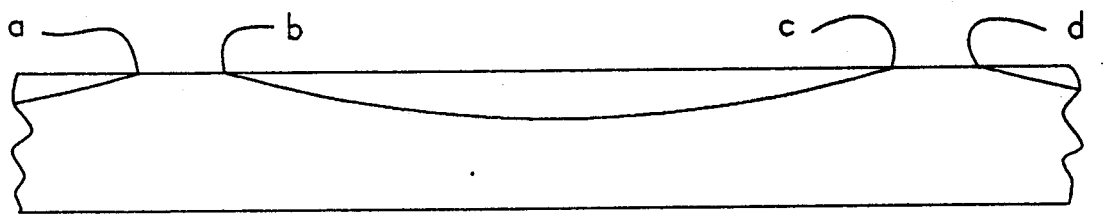
FIG. 4 is a cross-sectional view of a portion of the door showing the gasket retaining bar, and depicting a force to distance diagram between that portion of the door and the gasket retaining bar.
Figure 4:
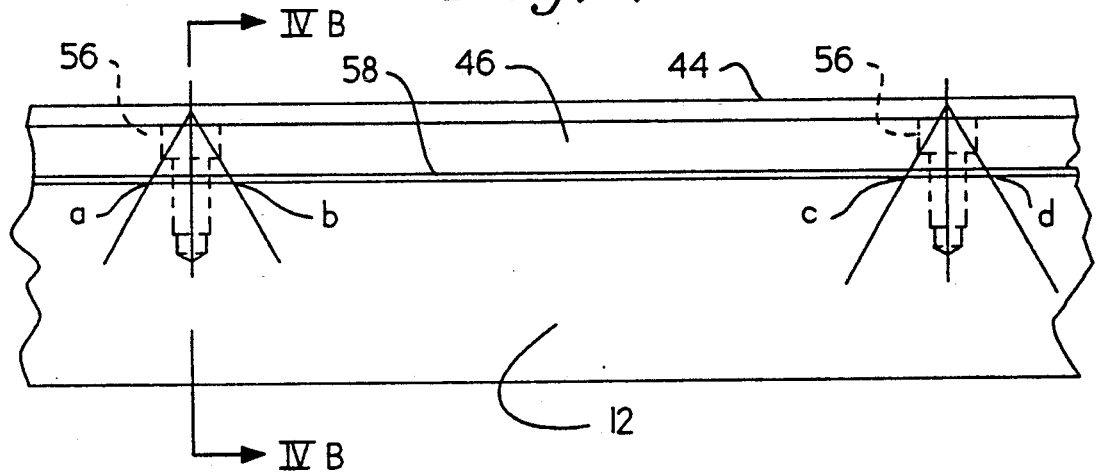
Figure 4B:
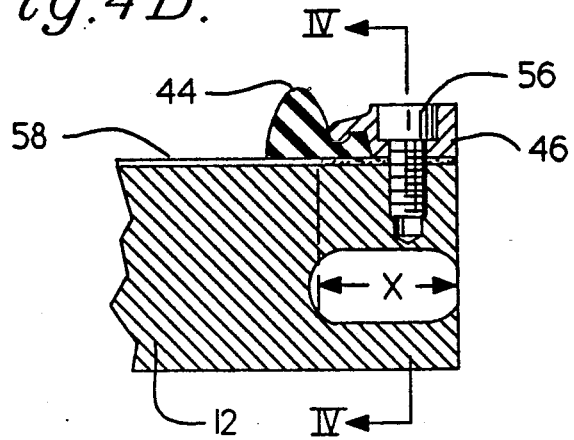

Referring now to FIG. 4, a cross-sectional view of the gasket retaining bar 46 as attached to the door 12 is shown. In particular, the gasket retaining bar 46 is attached to the inside face of the door 12 with multiple bolts 56. It should be appreciated that the amount of clamping force along the gasket retaining bar 46 depends on the proximity of that part of the gasket retaining bar 46 to a bolt 56. FIG. 4 includes a diagram of the relationship between the clamping force and the distance along the gasket retaining bar 46 between the bolts used to secure the gasket retaining bar 46 to the door 12. It has been found that the decrease in clamping force between the bolts 56 securing the gasket retaining bar 46 to the door 12 can be compensated for by the use of a sealant liquid between the inside door face and the gasket retaining bar 46 and gasket 44. More particularly, a sealant liquid such as Permatex Aviation's Form-a-Gasket is spread in about a one inch thick margin along the edge of the inner face of the door 12 as indicated by the dimension "X" in FIG. 4.

Figure 5:
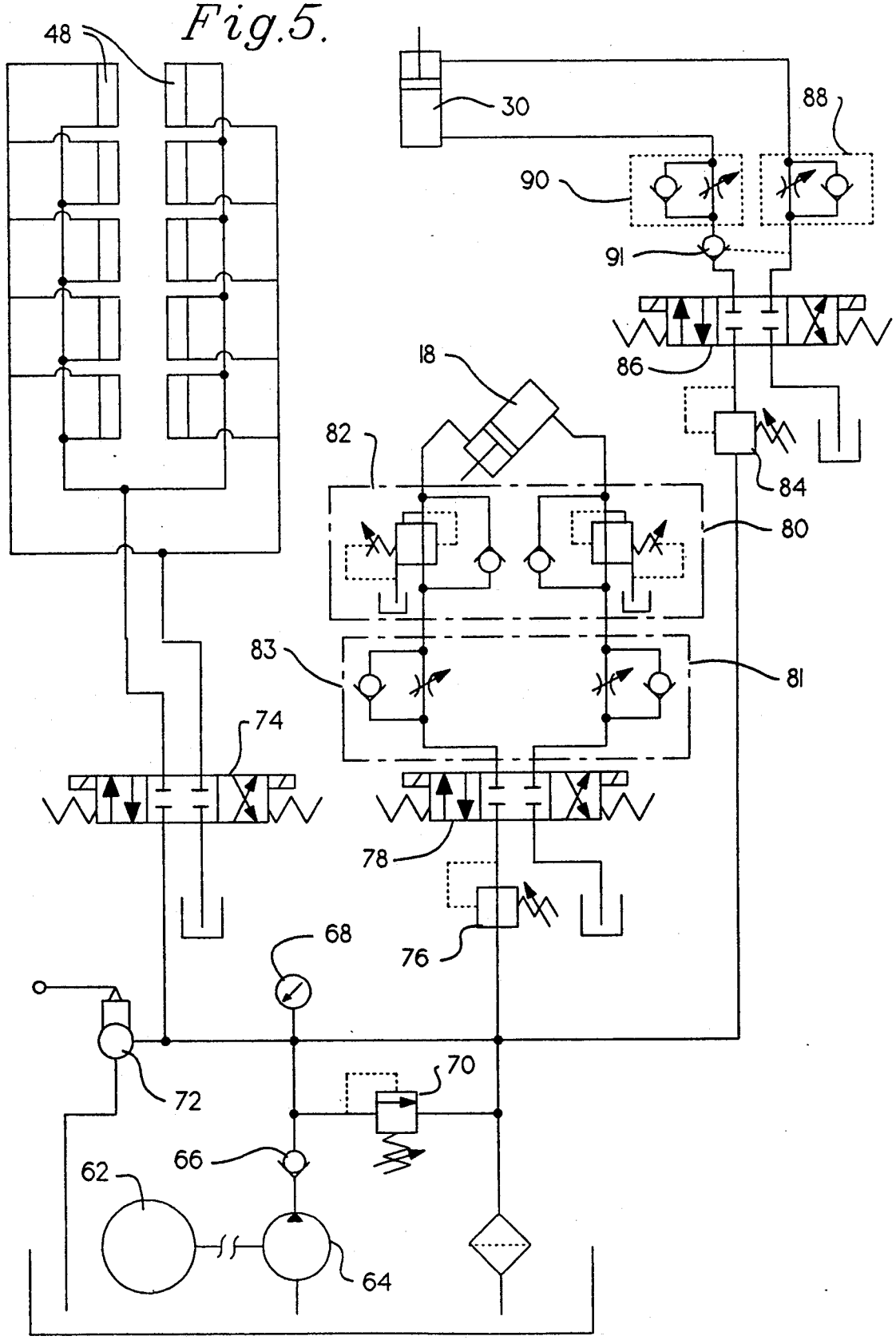
FIG. 5 is a schematic view of the hydraulic circuit used for controlling the clamping means, open-close cylinder, and raise-lower cylinder.

FIG. 5 depicts the hydraulic circuit which is used to control the clamping means, the open-close hydraulic cylinder, and the raise-lower hydraulic cylinder. The hydraulic circuit for the present invention generally includes three subcircuits, one each for the clamping means, the open-close hydraulic cylinder, and the raise-lower hydraulic cylinder. Each of these subcircuits is commonly provided with hydraulic pressure by a pump 66 driven by a motor 62 which provides hydraulic pressure to the overall circuit and each of the subcircuits. The pump includes a check valve 66 at its discharge and a pressure valve 68 for monitoring the pressure in the hydraulic circuit. In addition, a controller 70 is provided to regulate the overall pressure in the hydraulic circuit. The controller 70 is manually set to achieve a desired pressure in the overall hydraulic circuit. A manual hydraulic pressuring device 72 is also provided in the overall circuit to provide hydraulic pressure should electrical power fail.

Hydraulic pressure is provided to the clamps 48 via a solenoid valve 74. When solenoid valve 74 is set in the left actuated position, hydraulic pressure from the overall circuit is provided to the clamping mechanism of the clamps 48 and causes the clamp pins to extend and seal the door against the chamber. When it is desired to unseal the door from the chamber, the solenoid valve 74 is set in the right actuated position which provides hydraulic pressure to the release mechanism of the clamps 48 and causes the clamp pins to retract. It should be appreciated that the positive application of hydraulic pressure is required to move the clamp pins from either the clamped or unclamped positions. In the absence of positive hydraulic pressure, the clamp pins will remain in the state that they were most recently placed in. When not being used to open or close the clamping means, the solenoid valve 74 is set in a neutral position. If it is desired to increase the amount of pressure provided by the clamps to offset set or creep in the door gasket, the controller 70 may be adjusted to increase the overall pressure in the hydraulic circuit. The clamps 48 will then provide correspondingly increased pressure to seal the door to the chamber.

In addition, the clamps 48 can be operated during the failure of electrical power or failure of the pump 64 because the solenoid valve 74 has a float center which permits operation of the solenoid valve 74 when it is unpowered and hydraulic pressure can be applied through solenoid valve 74 by the manual hydraulic pressure device 72. In this manner, the clamps 48 can always be clamped or unclamped during losses of electrical power or failure of the pump 64.

Hydraulic pressure is supplied to the open-close hydraulic subcircuit by controller 76 and a solenoid valve 78. The controller 76 is used to set the pressure in the open-close hydraulic subcircuit at a desired level which may be different than the pressure in the overall hydraulic circuit. When solenoid valve 78 is set in the left actuated position, hydraulic pressure causes the open-close hydraulic cylinder 18 to extend which in turn causes the door to open. After the door 12 is opened, the solenoid valve 78 is set in a neutral position. The amount of force which is used to open the door may be adjusted using variable pressure reducing valve 80 in the open-close hydraulic subcircuit. By adjusting the opening force to a desired amount, it can be insured that the opening torque of the door is non-injurious.

When it is desired to close the door, the solenoid valve 78 is set to the right actuated position which provides hydraulic pressure to the open-close hydraulic cylinder 18 such that the cylinder is contracted. As in the case of opening the door, the closing force of the door may be adjusted by variable pressure reducing valve 82 to insure that a non-injurious closing torque is used. Typically, the variable pressure reducing valves 80 and 82 will be set such that a resistance caused by a person's arm inserted between the door and chamber will overcome the closing or opening pressure. The open-close hydraulic subcircuit additionally includes check valves 81 and 83. Check valves 81 and 83 provide protection against inadvertent opening or closing of the door over time by insuring that hydraulic pressure is not lost in the open-close hydraulic subcircuit due to leakage or gradual loss of pressure in the overall hydraulic circuit.

The hydraulic subcircuit for the raise-lower cylinder 30 is supplied with hydraulic pressure from the overall hydraulic circuit via controller 84 and solenoid valve 86. Controller 84 maintains the pressure of the raise-lower hydraulic subcircuit at a desired level which may be different from the pressure in the overall hydraulic circuit. Solenoid valve 86 is used to actuate the raise-lower hydraulic cylinder 30. When solenoid valve 86 is set in the right actuated position, hydraulic pressure is supplied to the raise-lower hydraulic cylinder 30 and causes the cylinder 30 to extend thereby raising the door. After the door is raised, the solenoid valve 86 is set to a neutral position. The amount of force used to raise the door is controlled by the variable flow control valve 88. When it is desired to lower the door, the solenoid value 86 is set in the left actuated position, and hydraulic pressure is supplied to hydraulic cylinder 30 and causes the cylinder to contract. The amount of force used to lower the door is controlled by variable flow control valve 90. As in the case of the open-close hydraulic subcircuit a check valve 91 has been included in the raise-lower hydraulic subcircuit to prevent inadvertent lowering of the door over time due to leakage from the overall hydraulic circuit.

The overall procedure for opening, closing, and sealing the door of the present invention is as follows:

When the door is in an open position, carts loaded with medical equipment are loaded into the sterilizer chamber as desired. The door is then closed by activating the pump of the overall hydraulic circuit and setting the solenoid valve for the open-close hydraulic subcircuit in a left actuated position. The open-close solenoid valve causes hydraulic pressure to be supplied to the open-close hydraulic cylinder which in turn causes the cylinder to contract and close the door against the face of the sterilizer chamber. The reducing pressure valve of the closing part of the open-close hydraulic subcircuit should be set such that minimal force is applied in closing the door. Minimal force in this context means that the force exerted on the door if it encounters a person's arm or other article will overcome the force provided to close the door by the open-close hydraulic cylinder.

Next the door is lowered into engagement with the clamps. This is accomplished by setting the raise-lower solenoid valve in the right actuated position which in turn supplies hydraulic pressure to the raise-lower hydraulic cylinder and causes it to contract. As the door is lowered, the ramps positioned adjacent to and above the pins of the clamps guide the door into proper position so that the door lugs are aligned with the clamps. The raise-lower solenoid valve is then set in a neutral position. The rate at which the door is lowered can be controlled by the variable flow control valve in the raise-lower hydraulic subcircuit.

Once the door has been positioned such that the door lugs are located next to the clamps, the door may be sealed. This is accomplished by setting the clamp solenoid valve in a right actuated position which supplies hydraulic pressure to the clamps and causes the pins of the clamps to extend against the door lugs and press the door against the sealing face of the sterilizer. This in turn compresses the compressible gasket on the inside face of the door against the sealing face of the sterilizer and thereby provides an airtight seal between the interior of the sterilizer and the external atmosphere. The clamp solenoid valve is then set in a neutral position. If the compressible gasket has suffered from creep or permanent set, the pressure used to compress the compressible gasket between the door and sealing face of the sterilizer can be increased by increasing the pressure setting on the controller for the overall hydraulic circuit.

The sterilizer is then cycled in its normal manner to sterilize the equipment which was loaded into the sterilizer.

After the sterilization cycle is complete, the sterilizer is unsealed by setting the clamp solenoid valve in the left actuated position. This causes hydraulic pressure from the overall hydraulic circuit to be supplied to the clamps such that the clamp pins are retracted and the pressure compressing the compressible gasket between the door and the sealing face of the sterilizer is released. The door is further unsealed by the action of spring pins which are located around the edge of the door and causes the door to displace slightly away from the sealing face of the sterilizer.

The door of the sterilizer is then raised by setting the raise-lower solenoid valve in the left actuated position. This in turn supplies hydraulic pressure to the raise-lower hydraulic cylinder such that the hydraulic cylinder extends and raises the door. The raise-lower solenoid valve is then returned to the neutral position. The force and rate at which the door is raised can be adjusted by the flow control valve for the raise portion of the raise-lower hydraulic subcircuit.

The door is then opened by setting the open-close solenoid valve in the left actuated position. This causes hydraulic pressure to be supplied to the open-close hydraulic cylinder such that it extends and causes the door to open. The open-close solenoid valve is then returned to its neutral position. The force exerted for opening the door by the open-close hydraulic cylinder is set at a minimal level by adjusting the pressure reducing valve for the open portion of the open-close hydraulic subcircuit. The term "minimal force" as used in this context is the same as was described for the closing procedure for the door of the sterilizer.

It should be appreciated that the detailed description of the preferred embodiments are illustrative of the invention. Other modifications and changes could be made by one skilled in the art without departing from the invention. For example, the opening, closing, and sealing apparatus of the invention can be adapted for use in autoclaves, sterilizers, or any other chamber in which it is desired to maintain an effective seal between the chamber and the external atmosphere.

What is claimed is:

1. Apparatus for opening, closing, and sealing a door of a chamber, said apparatus comprising:
   a) means for moving said door between an open and a closed position; and
   b) hydraulically activated means for clamping said door to said chamber, said clamping means providing clamping force such that an effective seal is provided between said door and said chamber, said clamping means comprising a plurality of extendable pins, said pins exerting variable clamping force when extended, said clamping force being proportional to hydraulic pressure supplied to said clamping means.

2. The apparatus of claim 1 wherein said extendable pins remain locked in an extended position unless hydraulic pressure is supplied to said clamping means to retract said pins.

3. Apparatus for opening, closing, and sealing a door of a chamber, said apparatus comprising:
   a) means for moving said door between an open and a closed position, said open-close moving means providing an adjustable force for moving said door between the open and closed positions; and
   b) means for clamping said door to said chamber, said clamping means providing clamping force such that an effective seal is provided between said door and said chamber.

4. The apparatus of claim 3 wherein said open-close moving means comprises a hydraulic cylinder with an extendable rod such that the force exerted by said rod in extending and retracting is proportional to hydraulic pressure supplied to said hydraulic cylinder.

5. Apparatus for opening, closing, and sealing a door of a chamber, said apparatus comprising:
   a) means for moving said door between an open and a closed position; and
   b) at least one hydraulically activated clamp fastened to said chamber for providing an adjustable clamping force proportional to hydraulic pressure supplied to said clamp effective for selectively moving said door and said chamber into and out of a sealed relationship.

6. The apparatus of claim 5 wherein said clamp comprises means for maintaining clamping force to maintain said sealed relationship between said door and said chamber notwithstanding the loss of hydraulic pressure to said clamp.

7. The apparatus of claim 6 wherein said means for maintaining clamping force is mechanical.

8. Apparatus for opening, closing, and sealing a door over an opening of a chamber, said apparatus comprising:
   a) means for moving said door between an open and a closed position;
   b) means for clamping said door to said chamber in a sealed relationship; and
   c) means for applying an adjustable force to move said door when said door is in a generally confronting relationship relative to the opening of said chamber between a first position out of engagement with said clamping means and a second position for engaging said clamping means.

9. The apparatus of claim 8 wherein said means for applying adjustable force comprises a hydraulic cylinder with an extendable rod such that the force exerted by said rod in extending and retracting is proportional to hydraulic pressure supplied to said hydraulic cylinder.

10. The apparatus of claim 8 further comprising means for guiding said door into engagement with said clamping means as said door is moved to the second position.

11. The apparatus of claim 10 wherein said clamping means is hydraulically activated and comprises a plurality of extendable pins, said pins exerting variable clamping force when extended, said clamping force being proportional to hydraulic pressure supplied to said clamping means, and said guiding means comprises a plurality of ramps positioned on said clamping means adjacent to a corresponding one of said pins such that as said door is moved into said second position each of said ramps aligns and moves said door towards said chamber.

12. Apparatus for opening, closing, and sealing a door of a chamber, said apparatus comprising:

a) means for opening and closing said door, said means providing adjustable force for opening and closing said door;

b) means for clamping said door to said chamber, said clamping means providing adjustable clamping force such that an effective seal is formed between said door and said chamber; and c) means for raising and lowering said door such that said door engages said clamping means in the lowered position, said means providing adjustable force for raising and lowering said door.

13. The apparatus of claim 12 wherein said clamping means comprises a plurality of extendable pins, said pins exerting variable clamping force when extended, said clamping force being proportional to hydraulic pressure supplied to said clamping means, said pins remaining locked in an extended position unless hydraulic pressure is supplied to said clamping means to retract said pins.

14. The apparatus of claim 13 wherein said door includes a plurality of door lugs, each of said lugs corresponding to one of said extendable pins such that said pins are extended against said lugs.

15. The apparatus of claim 14 further comprising means for guiding said door lugs into engagement with said extendable pins.

16. The apparatus of claim 15 wherein said guiding means comprises a plurality of ramps, each of said ramps being positioned above and adjacent to a corresponding one of said extendable pins such that as said door is moved into a lowered position said ramps align and move said door towards said chamber.

17. Apparatus for opening, closing, and sealing a door to a chamber, said apparatus comprising:

a) a first hydraulic cylinder operatively interconnected to said chamber and said door for opening and closing said door, said first hydraulic cylinder having an extendable rod operative for exerting a force against said door proportional to hydraulic pressure supplied to said first hydraulic cylinder;

b) a plurality of hydraulically activated clamps attached to said chamber, each of said clamps having an extendable pin, said pins exerting variable clamping force when extended by the application of hydraulic pressure to said clamps such that an effective seal is formed between said door and said chamber, said clamping force being proportional to hydraulic pressure supplied to said clamps; and c) a second hydraulic cylinder operatively interconnected to said chamber and said door for moving said door between a first and a second position, said second hydraulic cylinder having an extendable rod operative for exerting a force against said door proportional to hydraulic pressure applied to said second hydraulic cylinder.

18. The apparatus of claim 17 further comprising a compressible gasket which contacts both said door and said chamber when said door is clamped to said chamber.

19. The apparatus of claim 17 further comprising a means for supplying an independently adjustable amount of hydraulic pressure to each of said first and second hydraulic cylinders and said plurality of clamps.

20. A method for opening, closing, and sealing a door to a chamber, the method comprising the steps of:

a) supplying hydraulic pressure to a hydraulic cylinder interconnecting said door and said chamber in an adjustable amount effective for closing said door with a force proportional to the amount of hydraulic pressure supplied to said hydraulic cylinder;

b) supplying hydraulic pressure to a plurality of clamps fastened to said door in an adjustable amount effective for permitting said clamps to seal said door and said chamber, said clamping force being proportional to the amount of hydraulic pressure supplied to said clamps; and c) supplying hydraulic pressure to said hydraulic cylinder in an adjustable amount effective for opening said door with a force proportional to the amount of hydraulic pressure supplied to said hydraulic cylinder.

21. The method of claim 20 comprising the additional step of supplying hydraulic pressure to said clamps to deactivate said clamps.

22. The method of claim 20 further comprising the step of supplying hydraulic pressure to a second hydraulic cylinder in an adjustable amount effective for moving said door when said door is in a closed relationship relative to said chamber between a first position out of engagement with said clamps and a second position for engaging said clamps, said second hydraulic cylinder moving said door with a force proportional to the amount of hydraulic pressure supplied to said second hydraulic cylinder.

23. Apparatus for opening, closing, and sealing a door of a chamber, said apparatus comprising:

a) means for moving said door between an open and a closed position; and b) means for clamping said door to said chamber, said clamping means providing an adjustable clamping force which is effective for providing a seal between said door and said chamber.

* * * * *